(12) United States Patent
Steger et al.

(10) Patent No.: US 7,448,800 B2
(45) Date of Patent: Nov. 11, 2008

(54) CEILING SUPPORT FOR A MEDICO-TECHNICAL RADIATION SOURCE

(75) Inventors: Rainer Steger, Hausen (DE); Michael Brill, Erlangen (DE)

(73) Assignee: Hans Pausch GmbH & Co., Erlangen (DE)

( * ) Notice: Subject to any disclaimer, the term of this patent is extended or adjusted under 35 U.S.C. 154(b) by 623 days.

(21) Appl. No.: 10/531,418

(22) PCT Filed: Nov. 13, 2003

(86) PCT No.: PCT/EP03/12667

§ 371 (c)(1), (2), (4) Date: Oct. 7, 2005

(87) PCT Pub. No.: WO2004/043261

PCT Pub. Date: May 27, 2004

(65) Prior Publication Data

US 2006/0071138 A1    Apr. 6, 2006

(30) Foreign Application Priority Data

Nov. 14, 2002 (DE) ............................... 102 52 931

(51) Int. Cl.
*H05G 1/02* (2006.01)

(52) U.S. Cl. .................... 378/193; 378/194; 378/195; 378/196; 378/197; 248/317; 248/323; 248/327; 248/333; 248/669

(58) Field of Classification Search ............. 378/193, 378/194, 195, 196, 197; 248/317, 323, 326, 248/327, 328, 329, 330.1, 333, 334.1, 125.2, 248/298.1, 610, 646, 669, 336, 337, 338; 254/10.5, 277
See application file for complete search history.

(56) References Cited

U.S. PATENT DOCUMENTS

| | | | | | |
|---|---|---|---|---|---|
| 2,876,362 | A | * | 3/1959 | Foderaro | 378/194 |
| 3,175,085 | A | * | 3/1965 | Avery | 378/197 |
| 3,776,500 | A | * | 12/1973 | Foderaro | 248/333 |
| 3,986,697 | A | * | 10/1976 | Amor et al. | 248/333 |
| 4,041,320 | A | * | 8/1977 | Amor et al. | 378/194 |
| 4,410,175 | A | * | 10/1983 | Shamp | 482/69 |
| 4,677,273 | A | * | 6/1987 | Colegrove et al. | 219/121.13 |
| 5,602,889 | A | * | 2/1997 | Oldendorf et al. | 378/29 |
| 5,768,336 | A | * | 6/1998 | Khutoryansky et al. | 378/116 |
| 7,090,396 | B2 | * | 8/2006 | Boomgaarden | 378/196 |

FOREIGN PATENT DOCUMENTS

DE        87 06 358.1        5/1987

* cited by examiner

*Primary Examiner*—J. Allen Shriver
*Assistant Examiner*—Todd M. Epps
(74) *Attorney, Agent, or Firm*—Manabu Kanesaka

(57) ABSTRACT

The invention relates to a ceiling support for a medico-technical radiation source. The inventive support comprises a telescopic element (2) consisting of several tubes (3) which fit in each other and are connected to a compensation weight device of the radiation source connected to the free end (E) of said telescopic element (2) with the aid of a first cable (12). The inventive weight compensation device comprises a cable drum (11) for winding and unwinding said first cable (12), a helical winch (15) associated thereto and connected to a sliding element (8) by means a second cable, said sliding element being displaceable against a pressure spring (6). The radius of said helical winch (15) gradually reduces according to the increasing force of the pressure spring (6) in such a way that the compensation couple of the weight remains identical aside from the respective length of the telescopic element (2).

Figure 1:
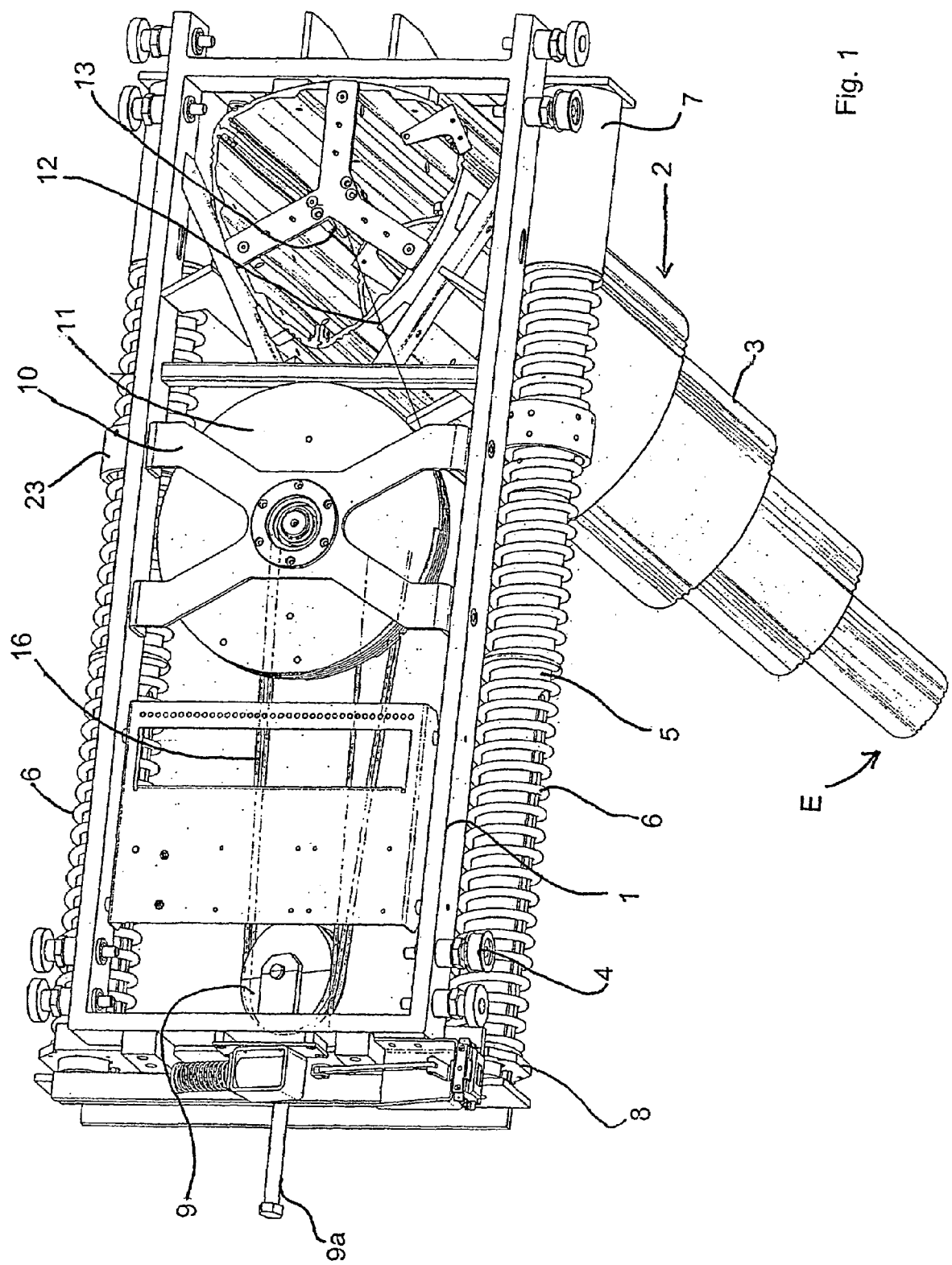

14 Claims, 5 Drawing Sheets ial Application No. PCT/EP 2003/012667, filed Nov. 13, 2003, and claims priority from, German Application No. 102 52 931.0, filed Nov. 14, 2002, the disclosure of which is hereby incorporated by reference herein in its entirety.

FIELD OF THE INVENTION

The invention relates to a ceiling support for holding a technical medical radiation source.

BACKGROUND OF THE INVENTION

Such a ceiling support is known for example from U.S. Pat. No. 3,175,085.

To compensate the weight of a radiation source installed on the free end of the telescope or telescope arm, a cable is usually led through the telescope arm which is connected with a device for the compensation of the weight. Such a unit can for example include a cable winch driven by an electro motor. With this, however, the radiation source cannot be moved with the dynamics of a manually adjustable ceiling support.

Furthermore, to compensate the weight, devices are known which include a gas pressure or torsion spring. Such units have the disadvantage that the weight compensation is not constant over the total extension length of the telescope arm. Torsion springs have the further significant disadvantage of a relatively short lifespan.

In addition, it is known that a helical tension spring is used for the weight compensation and the cable is led over the spiral winch. Although this can be used to achieve an almost constant compensation of the weight over a wide section of the extension length of the telescope arm, a ceiling support using helical tension springs cannot be designed compactly. Moreover additional technical safety devices must be provided in case the helical tension springs break.

SUMMARY OF THE INVENTION

Object of the invention is to specify a ceiling support to hold a technical medical radiation source which is designed as simply as possible, has a long lifespan and can be adjusted over a wide range to the particular weight of the radiation source.

This object is solved by the features of claim 1. Useful embodiments result from the features of claims 2 to 14.

According to the invention, a ceiling support is provided to hold a technical medical radiation source with a telescope made of several telescopable tubes, which telescope is connected via a first cable with a device for the compensation of the weight of a radiation source to be installed on the free end of the telescope, wherein the compensation device is comprised of:

a cable drum for winding and unwinding the first cable,
a spiral winch which is permanently connected with the cable drum,
   wherein the spiral winch is connected via a second cable with a sliding element which can be shifted against the force of a pressure spring, and
   wherein a radius of the spiral winch decreases with increasing pressure of the pressure spring so that a torque compensating the weight remains essentially the same regardless of the particular length of the telescope.

The term "cable" is used in connection with this invention generally in the sense of a means of connection which can be wound. To this extent the term "cable" also means the means of connection such as for example a chain, a metal or woven strip, a plastic belt, a plastic cable and similar. The exterior circumference of the "cable drum" and the "spiral winch" is each designed so that the particular "cable" being used can be wound up with this.

The suggested ceiling support is constructed simply. The suggested use of a pressure spring contributes to a significantly improved durability and operational safety. Moreover, this permits adjustment of the weight to be compensated within a wide range.

Preferably the spiral winch is installed firmly on the cable drum. In other words it cannot be turned in relation to the cable drum. In this case, the first and the second cable can also be replaced by a single cable which is connected on the one end with the telescope and on the other end with the movable sliding element. However, in this case, the cable is secured to the end of the cable drum and/or to the end of the spiral winch.

According to an advantageous embodiment, the decrease of the radius is not linear. It can run similar to a hyperbola. With this, an essentially constant compensation of the weight of the radiation source can be achieved over the entire extension range of the telescope arm. It is useful that the spiral winch can be designed in the shape of a hyperbolic spiral winch. With a hyperbolic form of the spiral winch, a constant weight compensation can be achieved in actual practice.

According to a further embodiment, two pressure springs are provided which are positioned on guide tubes running parallel to each other. The suggested arrangement of the pressure springs on guide tubes contributes to improved break resistance. Even when one of the pressure springs breaks, the radiation source does not suddenly fall and thus endanger persons.

It is advantageous that the sliding element is a crosshead which can be shifted on the guide tubes against the force of the pressure springs. It is useful that the second cable be wound around a roller installed on the crosshead, mounted with its one end to a frame holding the telescope arm and with its other end to the exterior radius of the spiral winch. The one end of the second cable can also be installed on an outside wall of the telescope arm. The compensation force exerted by the pressure springs via the crosshead on the spiral winch and thus on the cable drum, is cut in half by providing the roller as a loose roller based on the principle of the pulley.

It is furthermore advantageous that the spiral winch be installed between the two pressure springs. This can be used to achieve a particularly compact construction.

To increase operational safety, it is useful to provide two first and two second cables. Even when one of the cables breaks, the ceiling support remains totally operational. For reasons of technical safety, the spiral winch can in addition be connected with a permanent magnet brake such that the spiral winch is braked when a power failure occurs. Such a brake is usually only applied when the ceiling support is vertically adjusted. A radiation source held by the ceiling support can thus be additionally secured against an accidentally initiated vertical movement.

According to a further embodiment, a device is provided to set a pre-stress of the pressure spring/s exerted on the sliding element. This makes it possible to set a range in which the pressure springs exhibit an almost linear characteristic curve. In addition, a device for the stepless setting of the spring rate can be provided which is usefully formed as a clamping cuff/s which presses the pressure spring/s against the guide tube. This can be used to compensate a further weight area.

According to a particularly preferred embodiment, on an inner side several grooves are provided which axially undercut at least one of the tubes, and guide rails which have an essentially ridge-like form are secured via a screw connection with groove stones held in the grooves. It is useful to provide three grooves on the inner side of the tubes uniformly over their circumference. The suggested positioning of the guide rails on the inner side of the tubes significantly simplifies the mounting of the telescope arm. The guide rails can be shifted radially in a certain area while the tubes are being mounted and then be tensed up with the tubes.

BRIEF DRESCRIPTION OF THE DRAWING

Figure 2:
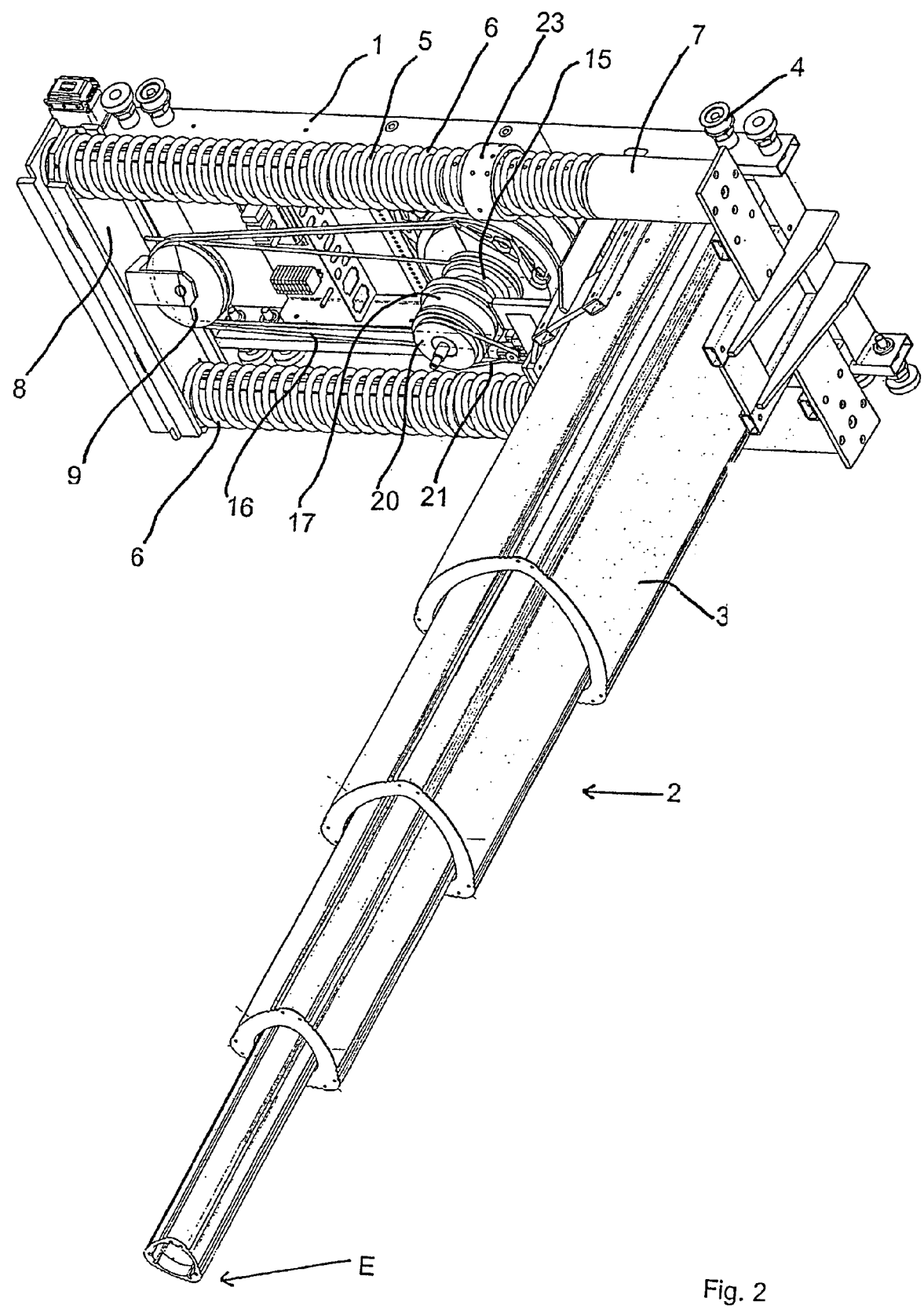
Figure 3:
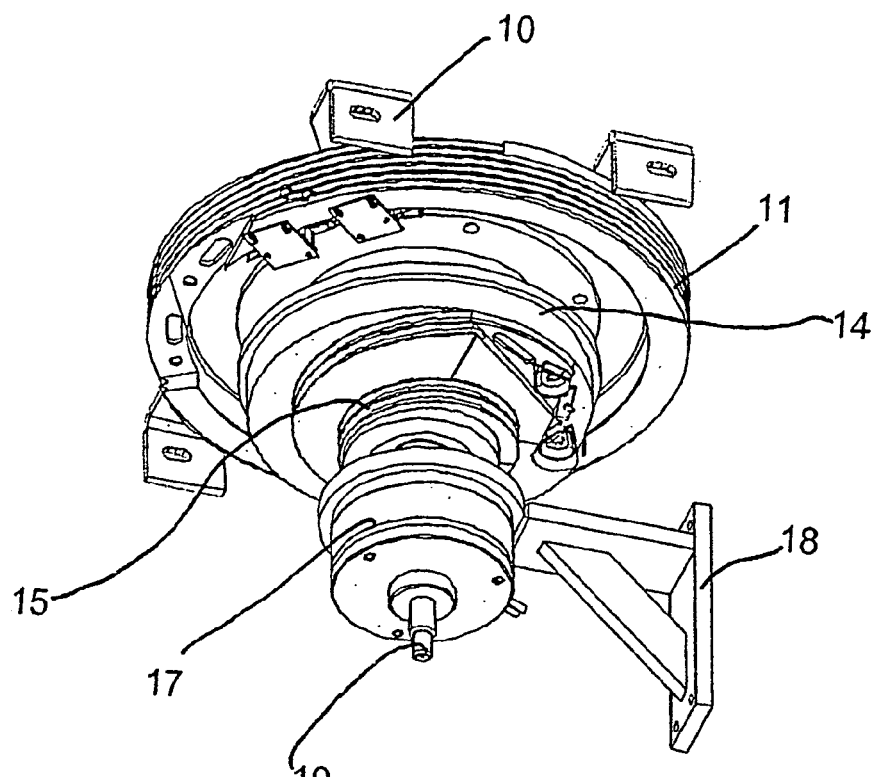
Figure 4:
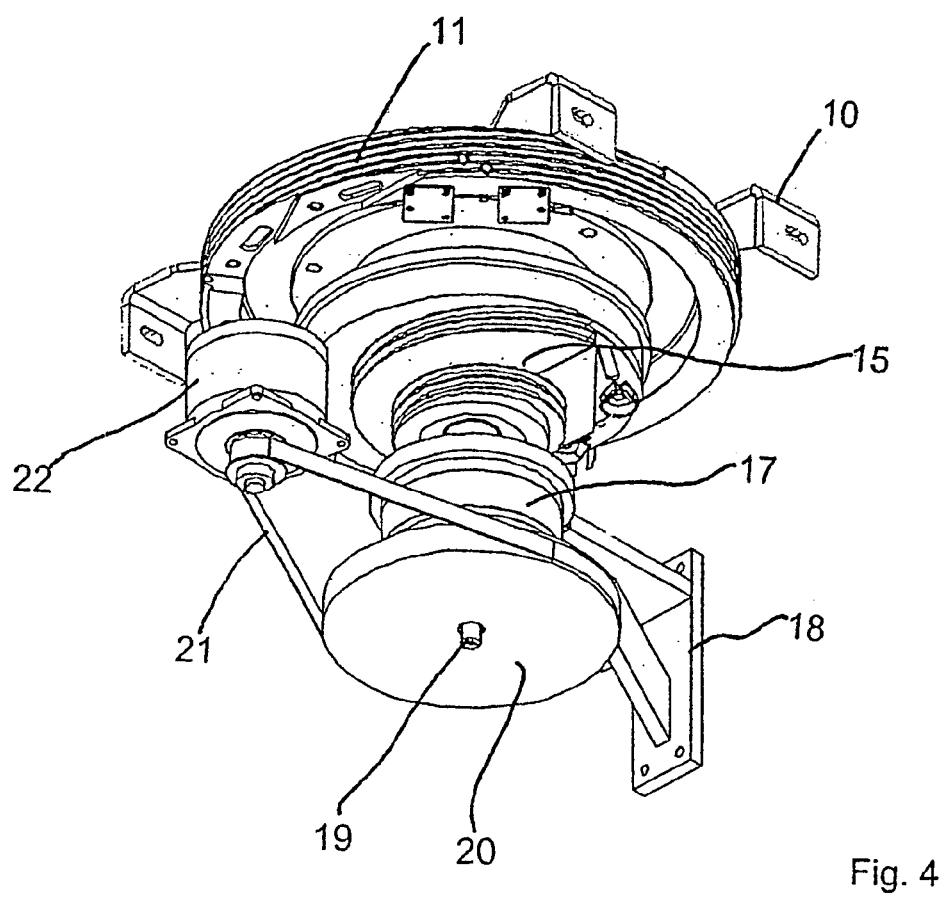
Figure 5:
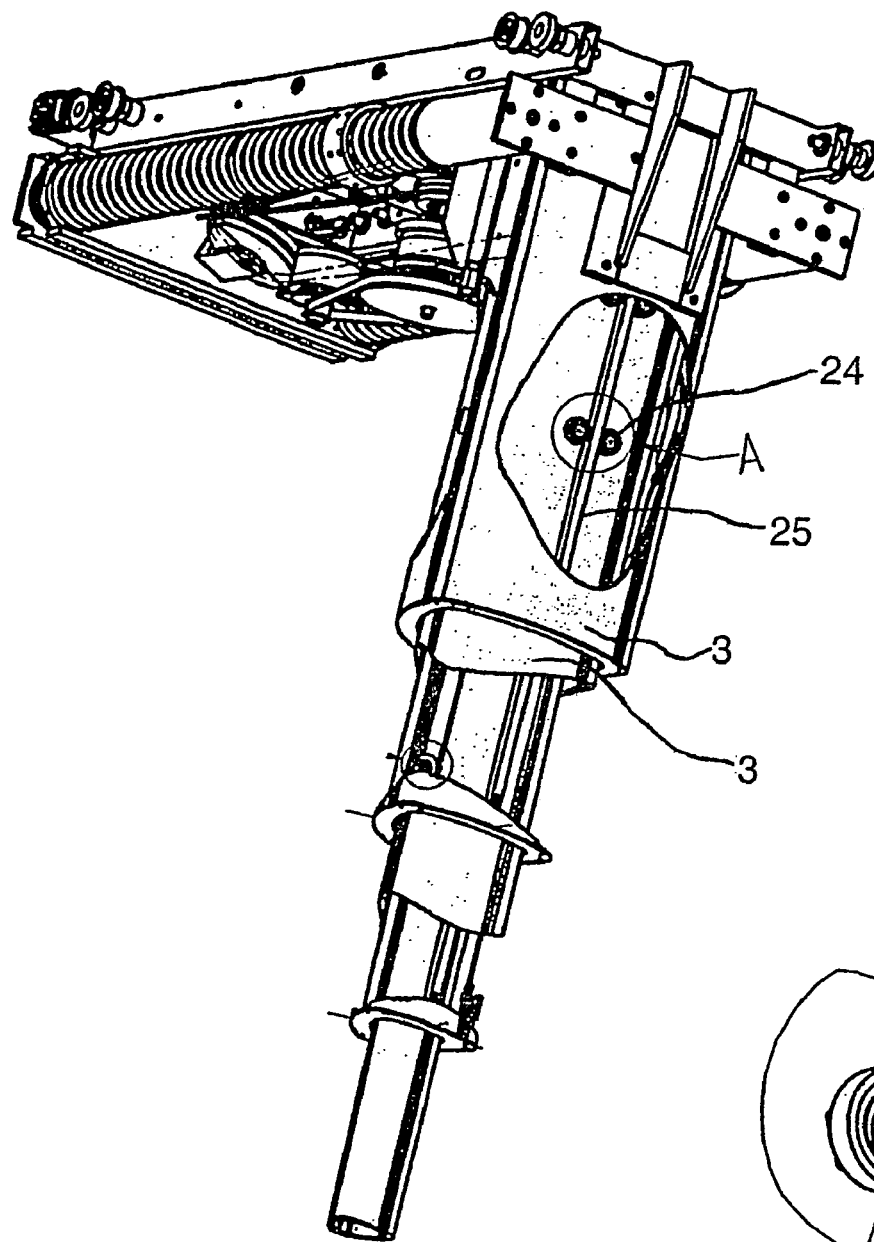
Figure 5A:
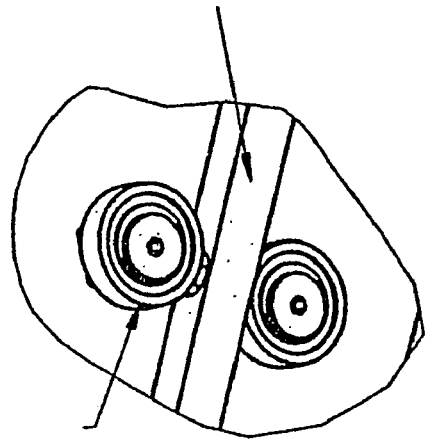
Figure 6:
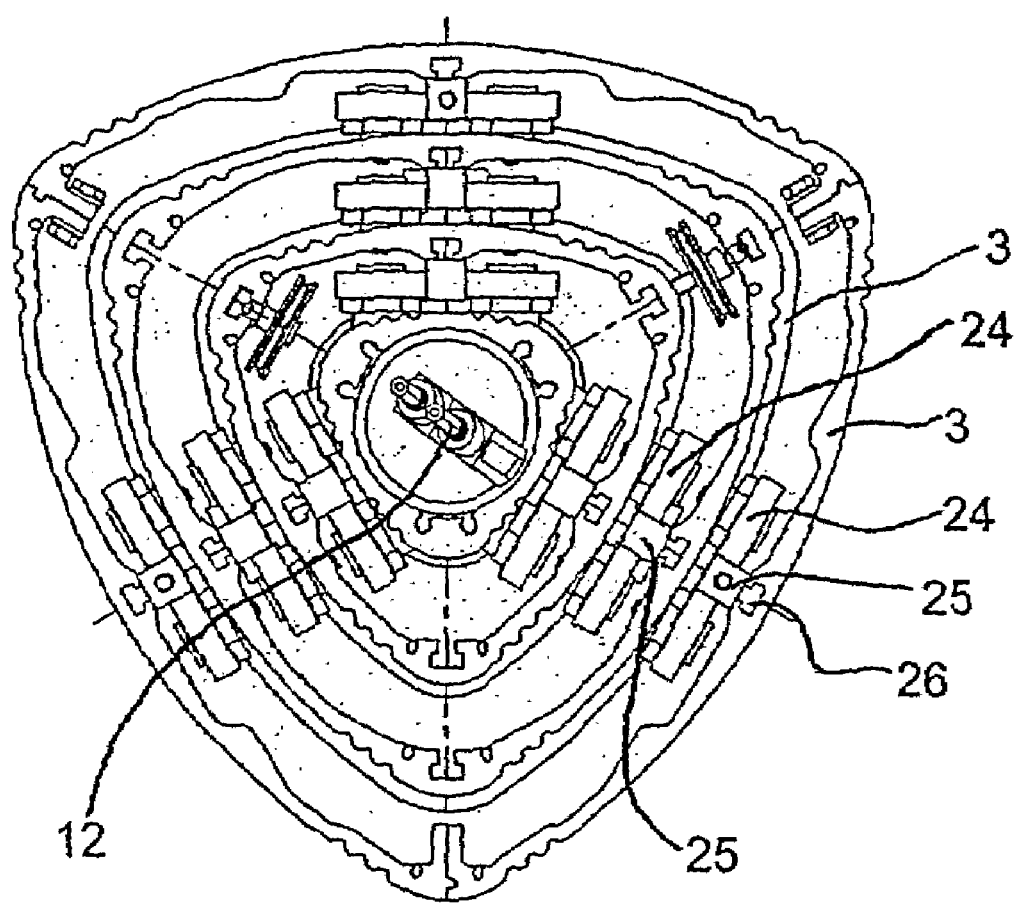

An example will now be used to describe the invention in more detail based on the drawing. The figures are listed below:

FIG. 1 A first view in perspective of the ceiling support,

FIG. 2 A second view in perspective of the ceiling support based on FIG. 1,

FIG. 3 A view in perspective of the spiral winch based on FIG. 2,

FIG. 4 A view in perspective of a spiral winch based on FIG. 3 with electro-motor drive, FIG. 5 A broken up view in perspective of the ceiling support, FIG. 5a A detail view according to section A of FIG. 5 and FIG. 6 A cross section view through the telescope arm.

DETAILED DESCRIPTON OF THE INVENTION

FIGS. 1 and 2 show a ceiling support in perspective as provided by the invention. In a rectangular frame 1, a telescope arm 2 approximately vertically extended thereto is installed which arm has several telescopable tubes 3. The frame 1 is equipped with rollers 4 with which it can move on rails (not shown here) installed on a ceiling of a room. It is useful that the tubes be made of extruded aluminum profiles. On the longitudinal sides of the frame 1 located opposite each other, guide tubes 5 are installed on which at least one—in this example two located next to each other—pressure springs 6 are positioned. The one end of the pressure springs 6 is supported against a sleeve 7 installed on each of the guide tubes 5, and the other end is supported against a slidable crosshead 8 installed on the guide tubes 5. A first deflection roller 9 which acts like a loose roller is installed in the middle on the side of the crosshead 8 which faces the telescope arm 2. The distance of the crosshead 8 to the axis of the cable drum 11 can be changed with an adjustment screw 9a. The adjustment screw 9a can thus be used to set the tension acting upon the crosshead 8. A support bar element 10 is mounted approximately in the middle of the frame 1 on which element a cable drum 11 is installed so that it can be turned. The exterior circumference of the cable drum 11 has guiding ridges to hold a first cable 12. The first cable 12 suggested schematically in FIG. 1 is led over a second, fixed deflection roller 13 and permanently connected (not shown here) with the tube 3 which forms the free end E of the telescope arm 2. Using a spacer disk 14, a hyperbolic spiral winch 15 is firmly connected with the cable drum 11 on the side facing away from the support bar element 10. The exterior circumference of the spiral winch 15 has guiding ridges for holding a second—in this example two second cables—cable 16. For the definition of a hyperbolic spiral, reference is made for example to BRONSTEIN-SEMENDJAJEW, Taschenbuch der Mathematik, 18th edition, 1979, page 92.

As can be seen in FIG. 2, the second cables 16 are secured with their one end in the vicinity of the maximum radius of the spiral winch 15 and with their other end on the exterior wall of the tube 3 (not shown here) installed on the frame 1. The second cables 16 are also wound around the first deflection roller 9.

A permanent magnet brake 17 which is firmly installed with a holder 18 on the frame 1 is permanently connected with the spiral winch 15. An axis 19 extending from the permanent magnet brake 17 can be optionally (see FIGS. 2 and 4) provided with a pulley 20 which is connected via a V-belt 21 with an electro motor 22 as the drive.

Clamping elements 23 with which the pressure springs 6 can be pressed against the guide tubes 5 are provided for setting the spring rate of the pressure springs 6. This can be used to steplessly set the length of the pressure springs 6 and to select the desired weight range to be compensated.

For the sake of clarity, FIGS. 1 and 2 show the ceiling support with fully extended telescope arm 2 and at the same time with non-compressed pressure springs 6. The functional relationship of the movable components of the ceiling support is not shown there.

The function of the ceiling support is as follows:

A radiation source (not shown here) which is installed on the free end E exerts a weight on the telescope arm 2. The weight is transmitted via the first cable 12 and the second deflection roller 13 to the cable drum 11. A constant torque corresponding to the weight is exerted on the cable drum 11 and the thereto permanently connected spiral winch 15. This constant torque is compensated by a counter torque exerted on the spiral winch 15. The counter torque is created by the pressure of the pressure springs 6 exerted on the crosshead 8 which is transmitted by the second cable 16. The pressure which is increasing with increasing compression of the pressure springs 6 is compensated by a non-linear reduction of the radius of the spiral winch 15 so that the counter torque is constant over the entire extension length of the telescope arm 2.

When the telescope arm 2 is completely extended, the pressure springs 6 are maximally compressed. The crosshead 8 is shifted by a maximum amount in the direction of the telescope arm 2. In this case, the second cables 16 are located on the minimal radius of the spiral winch 15. With upward movement of the telescope arm 2, the spiral winch 15 turns so that the second cables 16 are wound up by a constantly increasing radius. Thus during winding up, a continuously larger section of length of the second cable is wound up per unit of rotation angle of the spiral winch 15. This is accompanied by the simultaneously decreasing pressure of the pressure springs 6 so that the counter torque is held constant.

The permanent magnet brake 17 can be provided optionally to brake a shifting movement of the telescope arm 2. The brake is usefully designed so that the permanent magnet brake 17 brakes the spiral winch 15 when the power is interrupted. In case of a power failure, an undesired shifting movement of the telescope arm 2 cannot occur.

The spiral winch 15 can furthermore be connected via the axis 19 with an electro motor drive 20, 21, 22. Such an electro motor drive is used to support the shifting movement of the telescope arm 2.

The weight to be compensated can be set by adjusting the clamping jaws 23 steplessly within a wide range. This makes it possible to change the effective length of the pressure springs 6.

FIGS. 5, 5a and 6 show an particularly preferred embodiment of the guidance of the tubes 3. The particularly preferred embodiment of the tubes 3 described below can also be taken by itself for an independent invention. When the telescope arm 2 is mounted, the problem occurs in actual practice that the guide rails 25 provided on the inner side of the tubes must be precisely adjusted to compensate for manufacturing tolerances of the tubes 3. Otherwise, when the telescope arm 2 is extended, the rollers 24 running on the guide rails 25 will lift up. To ensure sufficient pretension of the rollers 24 against the edges of the guide rails 25, the rollers 24 must be secured eccentrically. They can be pre-tensioned against the guide rails 25 during mounting. According to the preferred example, axially undercutting grooves 26 are provided in the tubes 3. In the essentially triangular profile of the tubes 3 shown here, the grooves 26 run along the interior side of the tubes 3 approximately in the middle and are staggered by 120°. Groove stones (not shown here) provided with a threading to secure the guide rails 25 are threaded into the grooves 26. The guide rails 25 are then connected with the groove stones with a screw. For mounting, two tubes 3 are then telescoped, wherein the guide rails 25 which can still be shifted are secured on the interior side of the exterior tube 3. The rollers 24 are placed against the guide rails 25 in the system. Then the interior tube 3 is pushed into the exterior tube. Because of this, the guide rails 25 adjust themselves automatically. They then only need to be tightened.

REFERENCE DESIGNATION LIST

1 Frame
2 Telescope arm
3 Tube
4 Roller
5 Guide tube
6 Pressure spring
7 Sleeve
8 Crosshead
9 First deflection roller
10 Support bar element
11 Cable drum
12 First cable
13 Second deflection roller
14 Spacer disk
15 Spiral winch
16 Second cable
17 Permanent magnet brake
18 Holder element
19 Axis
20 Pulley
21 V-belt
22 Electro motor
23 Clamping jaws
24 Roller
25 Guide rail
26 Groove
E Free end

The invention claimed is:

1. A ceiling support for holding a technical medical radiation source,
with a telescope (2) made of several telescopic tubes (3), which is connected via a first cable (12) with a device for compensation of the weight of the radiation source to be in-stalled on the free end of the telescope (2),
wherein the device for compensation is comprised of:
a cable drum (11) for winding and unwinding the first cable (12),
a spiral winch (15) which is connected with the cable drum (11),
wherein the spiral winch (15) is connected via a second cable (16) with a sliding element (8) which can be shifted against the force of a pressure spring (6), and
wherein a radius of the spiral winch (15) decreases with in-creasing pressure of the pressure spring (6) so that a torque compensating the weight remains essentially constant regard-less of the particular length of the telescope (2).

2. The ceiling support as defined in claim 1, wherein the spiral winch (15) is installed firmly on the cable drum (11).

3. The ceiling support as defined in claim 1, wherein the decrease in the radius is not linear.

4. The ceiling support as defined in claim 1, wherein the spiral winch (15) is a hyperbolic spiral winch.

5. The ceiling support as defined in claim 1, wherein two pressure springs (6) are provided which are positioned on guide tubes (5) running parallel to each other.

6. The ceiling support as defined in claim 1, wherein the sliding element is a crosshead (8) which can be slid on the guide tubes (5) against the force of the pressure springs (6).

7. The ceiling support as defined in claim 1, wherein the second cable (16) is wound around a roller (9) installed on the crosshead (8), and is secured on its one end to a frame (1) holding the telescope (2) and with its other end at the maximum radius of the spiral winch (15).

8. The ceiling support as defined in claim 1, wherein the spiral winch (15) is installed between the two pressure springs.(6).

9. The ceiling support as defined in claim 1, wherein two first (12) and two second cables (16) are provided.

10. The ceiling support as defined in claim 1, wherein the spiral winch (15) is connected with a permanent magnet brake (17) such that the spiral winch (15) will be braked when there is a power failure.

11. The ceiling support as defined in claim 1, wherein the spiral winch (15) is connected with an electro motor drive (20, 21, 22).

12. The ceiling support as defined in claim 1, wherein a device (23) is provided for the setting of a pre-tension of the pressure spring/s (6) to be exerted on the sliding element (8).

13. The ceiling support as defined in claim 1, wherein a device for the stepless setting of the spring rate is provided which preferably is a clamping cuff (23) which presses the pressure spring (6) against the guide tube (5).

14. The ceiling support as defined in claim 1, wherein several axial undercut grooves (26) are pro-vided on one interior side of at least one of the tubes (3) so that essentially ridge-shaped guide rails (25) are mounted via a screw connection with the groove stones in the grooves (26).

* * * * *